United States Patent [19]

van Leuwen et al.

[11] 4,011,181

[45] Mar. 8, 1977

[54] POLYURETHANE FOAMS CONTAINING STANNOUS CATECHOL DERIVATIVES

[75] Inventors: Bruce G. van Leuwen, Trumbull; James J. Pitts, Hamden, both of Conn.

[73] Assignee: Olin Corporation, New Haven, Conn.

[22] Filed: July 30, 1975

[21] Appl. No.: 600,244

Related U.S. Application Data

[63] Continuation-in-part of Ser. No. 375,396, July 2, 1973, Pat. No. 3,899,520.

[52] U.S. Cl. .................. 260/2.5 AB; 260/2.5 AC; 260/414
[51] Int. Cl.² ................. C08G 18/24; C08G 18/14
[58] Field of Search ............... 260/2.5 AB, 2.5 AC, 260/414, 429.7

[56] References Cited

UNITED STATES PATENTS

| | | | |
|---|---|---|---|
| 3,036,022 | 5/1962 | Stewart | 260/2.5 AB |
| 3,060,137 | 10/1962 | Gemeinhardt | 260/2.5 AB |
| 3,267,047 | 8/1966 | Gmitter | 260/2.5 AB |
| 3,381,019 | 4/1968 | Morehouse | 260/2.5 AB |
| 3,899,520 | 8/1975 | van Leuwen | 260/2.5 AB |

FOREIGN PATENTS OR APPLICATIONS

| | | | |
|---|---|---|---|
| 948,191 | 1/1964 | United Kingdom | 260/2.5 AB |
| 927,004 | 5/1963 | United Kingdom | 260/2.5 AB |
| 876,434 | 8/1961 | United Kingdom | 260/2.5 AB |

*Primary Examiner*—C. Warren Ivy
*Attorney, Agent, or Firm*—James B. Haglind; Donald F. Clements; Thomas P. O'Day

[57] ABSTRACT

Polyurethane foams are prepared from compositions containing, as gel catalysts, a select group of stannous catechol derivatives.

17 Claims, No Drawings

POLYURETHANE FOAMS CONTAINING STANNOUS CATECHOL DERIVATIVES

This application is a continuation-in-part of U.S. application Ser. No. 375,396, filed July 2, 1973, now U.S. Pat. No. 3,899,520.

This invention relates to the preparation of polyurethane form compositions containing stannous catechol derivatives as gel catalysts.

It is known in the art that stannous catecholates are of utility generally as stabilizing agents for polymeric materials such as polybutadiene rubber. These catecholates can be prepared, according to the prior art, by reacting a tin compound, such as stannous dichloride or stannous oxide with a catechol as described for example in Emeleus and Zuckerman, *J. Organometal. Chem.*, Vol. 1, 328 (1964) and Cocks and Zuckerman, *Inorg. Chem.*, Vol. 4, 592 (1965). However, such prior art processes, along with requiring the use of a reaction catalyst and elevated temperatures and pressures, also require extended reaction times and in addition may require a burdensome neutralization step in the recovery of the reaction product. Thus a need still exists in this art for a simple, less costly method for preparing stannous catecholates.

It is also known in the art to utilize certain organo-tin compounds, or mixtures thereof, as gel catalysts in the preparation of polyurethane foam. For example, Japanese Patent No. 70-38,840, (as reported in Chemical Abstracts Vol. 76, 60494t, 1972) teaches a gelling catalyst for polyurethane foam consisting of a mixture of 2-ethylhexanoic acid, oxyditin (II) bis(2-alkylhexanoate), tin (II) bis(2-ethylhexanoate) and 4-tert-butylcatechol tin (II) salt. U.S. Pat. Nos. 3,391,091 and 3,198,757 teach other organo-tin compounds. The most commonly used organo-tin catalyst is stannous octoate. However, because of its hydrolytic instability, this material cannot be used in polyurethane foam forming systems or pre-blends which are subjected to prolonged storage in a moist environment.

It is a primary objective of the present invention to provide novel organo-tin compositions which are hydrolytically stable and useful as gel catalysts in the production of polyurethane foam.

Briefly, stannous catechol derivatives used as gel catalysts in the present invention are prepared by reacting, in the presence of a solvent, a stannous carboxylate with a catechol of formula I as follows:

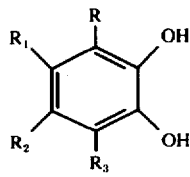

wherein each of R, $R_1$, $R_2$, and $R_3$ is independently selected from the group consisting of hydrogen, halogen, nitro, amino, nitroso, sulfonyl, alkyl having 1 to about 10 carbon atoms, and alkoxy having 1 to about 10 carbon atoms.

Any of the catechols represented by formula I may be used. Illustrative catechols include catechol, 3- and 4-methyl catechol, 3- and 4-tert-butyl catechol, 4-isopropyl catechol, 3,5- or 3,6-dimethyl catechol, 3,4,5,6-tetrachloro catechol, 3,4,5,6-tetrabromo catechol, 3- or 4-nitro catechol, 5-nitroso catechol, heptyl catechol, octyl catechol, sulfonyl catechol, 3-chloro-5-methyl catechol, 3,6-dibromo-4,5-dimethyl catechol, 3,5-diamino catechol, 3- or 5-methoxy catechol, 3-ethoxy catechol, 3-pentyloxy catechol, 3,5-dinitro catechol, 4-amino-5-bromo catechol, 3,4,6-tribromo-5-methyl catechol, 3-methoxy-5-nitro catechol, tetrafluoro catechol, 4-(2-aminopropyl)-3-chloro catechol and 4-bromo-5-nitro catechol.

However, it is preferred to employ catechols of formula I wherein each of R, $R_1$, $R_2$, $R_3$ is independently selected from the group consisting of hydrogen, chlorine, bromine, nitro, alkyl having 1 to about 4 carbon atoms and alkoxy having 1 to 4 carbon atoms. Illustrative examples of these are catechol, 3- and 4-methyl catechol, 3- and 4-tert-butyl catechol, 3,4,5,6-tetrabromo catechol, 3- or 4-nitro catechol, 3-chloro-5-methyl catechol, 3,4,6-tribromo-5-methyl catechol, 3-methoxy catechol, and 4-bromo-5-nitro catechol.

The stannous carboxylate reactant used can be any compound represented by formula II as follows:

$$(R_4COO)_2 Sn \qquad II$$

wherein $R_4$ represents hydrogen, alkyl having from 1 to about 9 carbon atoms, or alkenyl having from 1 to about 9 carbon atoms. Illustrative examples include stannous formate, stannous acetate, stannous pentanoate, stannous butyrate, stannous acrylate, stannous methacrylate, stannous hexanoate, stannous butenoate, stannous pentenoate, stannous heptanoate, stannous hexenoate, stannous octanoate, stannous 2-ethyl hexanoate, stannous sorbate, stannous nonanoate, and stannous decanoate.

Preferred stannous carboxylate reactants are those in which $R_4$ represents an alkyl group having from about 5 to about 9 carbon atoms. Illustrative examples include stannous hexanoate, stannous octanoate and stannous 2-ethyl hexanoate.

The reaction is carried out in the presence of an inert organic solvent. By inert is meant that the solvent does not contain any moieties which may interfere with the reaction process. Any such liquid compound which is a solvent for one or both reactants, or a mixture of solvents, may be used. Typical examples of suitable solvents include diethyl ether, methanol, ethanol, isopropanol, acetone, dioxane, dimethylsulfoxide, tetrahydrofuran, methyl ethyl ketone, dimethyl formamide and toluene among others. To facilitate product recovery and purification, it is preferable to use a solvent having a low boiling point, e.g., at from about 30° to about 90° C and preferably below 50° C and in which the product is relatively insoluble, such as diethyl ether.

Any suitable amount of solvent may be employed in the reaction. Usually a sufficient amount of solvent or solvent mixture is used to dissolve each of the reactants independently. For example, the molar ratio of solvent to total reactants is from about 0.5:1 to about 100:1 preferably from about 1:1 to about 10:1.

The reaction may be carried out at any suitable temperature, for example, temperatures ranging from about 0° to about 100° C. However, since the reaction proceeds satisfactorily without heat, it is preferred, from a practical standpoint, to carry out the reaction at close to ambient or room temperature such as from about 20° to about 40° C.

Although the reaction is suitably conducted at atmospheric pressure, higher or lower pressures may be used if desired.

In carrying out the reaction between the stannous carboxylate and the catechol compound, any molar ratio of stannous carboxylate to catechol may be employed, such as from about 0.1:1 to about 10:1 and preferably about 0.6:1 to about 6:1. As a practical matter, the most preferred proportions are stoichiometric molar proportions, i.e., about 1:1.

Any suitable order of mixing the reactants and the solvent may be used in carrying out the process of the invention. For example, each reactant may first be individually dissolved in the desired solvent and thereafter the two solutions placed, simultaneously or in order of addition, in a reaction vessel where reaction proceeds. Although continuous agitation is not necessary, it is preferred in order to reduce reaction time and insure complete reaction.

The reaction proceeds rapidly, being completed in less than about 4 hours and more usually in about 10–40 minutes.

The reaction product is readily recovered from the reaction mixture by filtration and thereafter easily purified by washing with an inert organic solvent such as diethyl ether.

Utilizing the above process, novel stannous catechol derivatives are produced which are useful as gel catalysts in the production of polyurethane foam by the process of the present invention. These novel derivatives are represented by formulas III and IV:

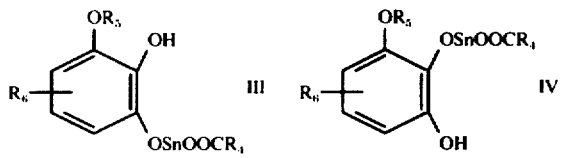

wherein $R_5$ represents alkyl having from 1 to about 10 carbon atoms, $R_4$ is as defined above and $R_6$ represents hydrogen, halogen, nitro or alkyl having 1 to about 10 carbon atoms.

The novel compounds can be any compounds illustrated by formulas III and IV, for example, [2-hydroxy-3-ethoxyphenolato (1-)] tin (II) acetate, [3-butoxy-2-hydroxy-4-nitrophenolato (1-)] tin (II) hexanoate, [2-hydroxy-5-chloro-6-methoxyphenolato (1-)] tin (II) butyrate, [3-isopropoxy-2-hydroxyphenolato (1-)] tin (II) decanoate, [2-hydroxy-3-methoxyphenolato (1-)] tin (II) octanoate, [2-hydroxy-6-methoxyphenolato (1-)] tin (II) ethyl hexanoate, [2-hydroxy-3-ethoxyphenolato (1-)] tin (II) hexanoate, [2-hydroxy-6-methoxyphenolato (1-)] tin (II) octanoate and [2-hydroxy-6-methoxyphenolato (1-)] tin (II) ethyl hexanoate.

However, preferred are those compounds of formulas III and IV wherein $R_5$ represents alkyl having from 1 to 4 carbon atoms, $R_4$ represents an alkyl group having from 5 to about 9 carbon atoms and $R_6$ represents hydrogen. Illustrative examples include [2-hydroxy-3-methoxyphenolato (1-)] tin (II) 2-ethyl hexanoate, [2-hydroxy-3-methoxyphenolato (1-)] tin (II) 2-ethyl hexanoate, [2-hydroxy-6-methoxyphenolato (1-)] tin (II) octanoate and [2-hydroxy-3-ethoxyphenolato (1-)] (II) hexanoate.

Further, it has been found that the above process produces other stannous catechol derivatives which are useful as gel catalysts in the process of the invention for the preparation of polyurethane foam. In accordance with this embodiment of the invention any such stannous catechol derivatives may be employed in foam production. This includes the derivatives represented by formulas III and IV above as well as derivatives represented by formula V as follows:

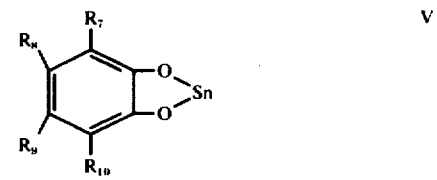

wherein each of $R_7$, $R_8$, $R_9$, and $R_{10}$ independently represents hydrogen, halogen, amine, nitro, nitroso, sulfonyl, and alkyl having 1 to about 10 carbon atoms. So far as compounds of formula V are concerned, it is preferred to employ those compounds in which each of $R_7$, $R_8$, $R_9$ and $R_{10}$ independently represents hydrogen, halogen, nitro and alkyl having from about 1 to about 4 carbon atoms.

Illustrative examples of the preferred embodiments of formula V include [1,2-benzenediolato (2-)] tin (II), [3-and 4-methyl-1,2-benzenediolato (2-)] tin (II), [tert-butyl 1,2-benzenediolato (2-)] tin (II), [3,4,5,6-tetrabromo-1,2-benzenediolato (2-)] tin (II), [4-nitro 1,2-benzenediolato (2-)] tin (II), [3,4-dimethyl-1,2-benzenediolato (2-)] tin (II) and [3-methyl-4-tert-butyl-1,2-benzenediolato (2-)] tin II.

More preferably, those compounds of formula V are employed in which each of $R_7$, $R_8$, $R_9$ and $R_{10}$ independently represents hydrogen, chlorine, bromine, nitro, and alkyl having from 1 to about 3 carbon atoms.

As noted above, the compounds of formulas III, IV, and V, or mixtures thereof, are useful as gel catalysts in the production of polyurethane foams, particularly flexible foams. In preparing polyurethane foam in accordance with the invention either the so called "one-shot method" or the "semi-prepolymer technique" ("quasi-prepolymer" technique) may be employed. Any combination of polyol components including polyester polyols or polyether polyols, organic polyisocyanate, blowing agent, blowing catalyst, and gel catalyst and other reactants capable of forming a cellular material can be used. It is well known in the art, for example, to prepare flexible polyurethane foam-forming formulations comprising a polyether polyol component having a hydroxyl number of less than about 250, an organic polyioscyanate, a blowing agent and a catalyst. Typical formulations are described in U.S. Pat. Nos. 3,072,582, issued Jan. 8, 1963, and No. 3,437,804, issued Oct. 17, 1967, and in Canadian Pat. No. 705,938, issued Mar. 16, 1965.

While, as indicated above, both polyether and polyester polyols can be employed in the practice of this invention, preferred embodiments utilize polyether polyols in the preparation of the polyurethane foam forming reaction mixture. Any suitable polyether polyol may be used for this purpose. These polyether polyols usually have a hydroxyl number for example from about 25 to about 800.

The polyether polyols include for example oxyalkylated polyhydric alcohols having a molecular weight range of about 200 to about 10,000, preferably between about 250 to about 8,000 more preferably between about 2,000 to about 7,000. These oxyalkylated polyhydric alcohols are generally prepared by methods well known in the art such as reacting, in the presence of an alkaline catalyst, a polyhydric alcohol and an alkylene oxide such as ethylene oxide, propylene oxide, butylene oxide, amylene oxide, epichlorohydrin, and mixtures of these alkylene oxides, using either random or step-wise addition.

Polyhydric alcohols suitable for use in preparing the polyether polyols include ethylene glycol, pentaerythritol, methyl glucoside, propylene glycol, 2,3-butylene glycol, 1,3-butylene glycol, 1,5-pentane diol, 1,6-hexane diol, glycerol, trimethylolpropane, sorbitol, sucrose, dextrose, mixtures thereof and the like. If desired, a portion of all of the polyhydric alcohol may be replaced with another compound having at least two reactive hydrogen atoms, such as alkyl amines, alkylene polyamines, cyclic amines, amides and polycarboxylic acids. Suitable alkyl amines and alkylene polyamines include methylamine, ethylamine, propylamine, butylamine, hexylamine, ethylenediamine, 1,6-hexanediamine, diethylenetriamine, and the like. Also, such cyclic amines as piperazine, 2-methylpiperazine and 2,5-dimethylpiperazine can also be used. Amides, such as acetamide, succinamide and benzenesulfonamide, constitute a further class of such reactive hydrogen compounds. A still further class of such reactive hydrogen compounds is the di- and polycarboxylic acids, such as adipic acid, succinic acid, glutaric acid, aconitic acid, diglycollic acid and the like. It will be recognized that the reactive hydrogen compound can be one containing different functional groups having reactive hydrogen atoms, such as citric acid, glycollic acid, ethanolamine and the like. Aromatic polyamines such as toluene diamine may also be employed. Mixtures of oxyalkylated polyhydric alcohols are also suitable for use in the process of this invention.

The organic polyisocyanates used in the preparation of the polyurethane foams include toluene diisocyanate, such as the 80:20 mixture or the 65:35 mixture of the 2,4- and 2,6-isomers, ethylene diisocyanate, propylene diisocyanate, methylene-bis-4-phenyl isocyanate, 3,3'-bitoluene-4,4'-diisocyanate, hexamethylene diisocyanate, naphthalene-1,5-diisocyanate, polyphenylene polymethylene isocyanate, mixtures thereof and the like. The preferred organic polyisocyanate is toluene diisocyanate. The amount of isocyanate employed in the process of this invention should be sufficient to provide at least about 0.7 NCO group per hydroxyl group present in the reaction system, which includes the polyol as well as any additive or foaming agent employed. An excess of isocyanate compound may be conveniently employed; however, this is generally undesirable due to the high cost of the isocyanate compounds. It is preferable, therefore, to employ sufficient isocyanate to provide no greater than about 1.25 NCO groups per hydroxyl group, and preferably between about 0.9 and about 1.15 NCO groups per hydroxyl group. The ratio of NCO to OH groups times 100 is referred to as the "index".

The polyurethane foams are prepared in the presence of a foaming agent which may be any of those known to be useful for this purpose. Illustrative are water and organic foaming agents containing up to about seven carbon atoms such as the halogenated hydrocarbons, lower molecular weight alkanes, alkenes, ethers and mixtures thereof. Typical halogenated hydrocarbons include, but are not limited to: monofluorotrichloromethane, dichlorofluoromethane, difluorodichloromethane, 1,1,2-trichloro-1,2,2-trifluoroethane, dichlorotetrafluoroethane, ethyl chloride, methylene chloride, chloroform, and carbon tetrachloride. Other useful foaming agents include lower molecular weight alkanes, alkenes and ethers such as methane, ethane, ethylene, propane, propylene, pentane, hexane, heptane, ethyl ether, diisopropyl ether, mixtures thereof and the like. The amount of foaming agent employed may be varied within a wide range. Generally, however, the halogenated hydrocarbons are employed in an amount from about 1 to about 50, and preferably about 5–35, parts per 100 parts by weight of the polyol, and generally water is employed in an amount from about 1.0 to 6.0 parts by weight per 100 parts by weight of the polyol.

The polyurethane foams may be prepared in the presence of a catalytic amount of a blowing catalyst. The catalyst employed may be any of the catalysts known to be useful for this purpose, such as tertiary amines. Typical tertiary amines include, but are not limited to, the following: 1,4-diazabicyclo [2,2,3] octane, i.e., triethylene diamine, N-hydroxyethyl morpholine, triethylamine, trimethylamine and mixtures thereof. Any catalytic proportion of blowing catalyst may be employed such as between about 0.1 and about 3.0 percent, and preferably between about 0.5 and about 2.5 percent, by weight of the polyol.

It is preferred in the preparation of the polyurethane foams of the present invention to employ minor amounts of a conventional surfactant in order to further improve the cell structure of the polyurethane foam. U.S. Pat. No. 2,834,748 and T. H. Ferrigno, *Rigid Plastic Foams* (New York: Reinhold Publishing Corp., 1963) pages 38–42, disclose various surfactants which are useful for this purpose. Generally up to 2 parts by weight of the surfactant are employed per 100 parts of the polyol.

In utilizing the stannous catechol derivatives of formulas III, IV and V as described above as gel catalysts in the process of the present invention for producing polyurethane foam, they are added to the polyurethane foam-forming mixture prior to foaming. Conveniently they are first blended with the polyol component used in making the foam and the blend is then added to the other ingredients of the polyurethane foam-forming reaction mixture. These derivatives can be used in any proportion which is effective as a gel catalyst in the production of polyurethane foam. For example, the gel catalyst may be employed in an amount from about 0.01 to about 5.0, and preferably from about 0.1 to about 2.0, parts by weight per 100 parts of polyol, which is used in preparing the foam.

The stannous catechol derivatives are generally insoluble in materials normally used in the production of polyurethane foams, for example, polypropylene glycols, polyethylene glycols, dioctylphthalate, water, toluene diisocyanate, trichloromonofluoromethane, dimethylsulfoxide, and dimethyl formamide. Thus they can be used in foam forming formulations containing such materials without the need to employ these catalysts in excess which might otherwise be necessary to compensate for losses due to interaction with, or dissolution in, these materials. These compounds also exhibit thermal stability up to about 300° C and they are hydrolytically stable in the presence of moisture. Consequently, they are particularly suitable for use in polyurethane systems which require long storage times or stability in the presence of moisture.

The following examples are presented to further illustrate the invention without any intention to be limited thereby. All parts and percentages are by weight unless otherwise specified.

EXAMPLE 1

Preparation of [1,2-benzenediolato (2-) ] tin (II).

To a reaction vessel containing a solution of 405 g. of stannous octanoate in 500 ml. anhydrous ether at 20° C was added rapidly with stirring, 110 g of catechol in 500 ml. of anhydrous ether and a precipitate was immediately formed. The solution was stirred for 15 minutes to insure complete reaction and filtered. A white crystalline solid was recovered which was washed by adding the solid to a reaction vessel containing about 500 ml. of ether and stirring the mixture. After filtration and drying, 224 g. (98% of theory) of product was obtained.

Analysis calculated for $C_6H_4O_2Sn$: Percent C, 31.76; H, 1.78; Found: Percent C, 31.41; H, 1.91.

EXAMPLE 2

Preparation of [4-methyl-1,2-benzenediolato (2-)] tin (II).

The procedure of Example 1 was used to react 12.4 g. of 4-methyl catechol in anhydrous ether with 40.5 g. of stannous octanoate in anhydrous ether to yield 23.82 g. (98% of theory) of purified [4-methyl-1,2-benzenediolato (2-)] tin (II).

Analysis calculated for $C_7H_6O_2Sn$: Percent C, 34.80; H, 2.51; Found: Percent C, 33.85; H, 2.47.

EXAMPLE 3

Preparation of [3-methyl-1,2-benzenediolato (2-)] tin (II).

A solution of 40.5 g. of stannous octanoate in anhydrous ether was reacted with 12.4 g. of 3-methyl catechol in anhydrous ether as described in Example 1. Total reaction time was about 20 minutes. A purified product weighing 21.8 g. (91% of theory) was obtained.

Analysis calculated as $C_7H_6O_2Sn$: Percent, 34.89; H, 2.51; Found: Percent C, 33.64; H, 2.54.

EXAMPLE 4

Preparation of [3,4,5,6-Tetrabromo-1,2-benzenediolato (2-)] tin (II).

Using the procedure of Example 1, 42.7 g. of 3,4,5,6-tetrabromocatechol in anhydrous ether and 40.5 g. of stannous octoate in anhydrous ether were reacted. As a product, 52.7 g. of [3,4,5,6-tetrabromo-1,2-benzenediolato (2-)] tin (II) was obtained.

Analysis calculated as $C_6Br_4O_2Sn$: Percent C, 13.27; Br, 58.9; Found: Percent C, 14.06; Br, 57.4.

EXAMPLE 5

Preparation of [tert-Butyl-1,2-benzenediolato (2-)] tin (II).

To a reaction vessel containing 40.5 g (0.1 mole) of stannous octanoate in 300 ml. of anhydrous ether was added rapidly with stirring 16.6 g. of tert-butyl catechol in 100 ml. of anhydrous ether. A voluminous precipitate was immediately formed. The mixture was stirred for 30 minutes, filtered, washed several times with ether and dried. A white solid product was obtained weighing 27.2 g. (95.4% of theory).

Analysis calculated as $C_{10}H_{12}O_2Sn$: Percent C, 42.43; H, 4.28; Found: Percent C, 42.30; H, 4.30.

EXAMPLE 6

Preparation of [4-nitro-1,2-benzenediolato (2-)] tin (II).

Using the procedure of Example 5, anhydrous ether solutions of 7.75 g. of 4-nitro catechol and 20.3 g. of stannous octanoate were reacted to yield 10.9 g. (98% of theory) of purified product.

Analysis calculated as $C_6H_3NO_4Sn$: Percent C, 26.50; H, 1.11; N, 5.15; Found: Percent C, 26.13; H, 1.57; N, 3.61.

EXAMPLE 7

Preparation of [Hydroxy methoxy phenolato (1-)] tin (II) octanoate.

Using the procedure of Example 5, a solution of 14. g. of 3-methoxy catechol in ether and a solution of 40.5 g. of stannous octanoate were reacted at 20° C to give 25.8 g. of a product which was filtered, washed several times with ether and dried. Analysis by nuclear magnetic resonance determined the product to be a mixture containing 95% [2-hydroxy-3-methoxy-phenolato (1)] tin (II) octanoate and 5% [2-hydroxy-6-methoxy phenolato (1)] tin (II) octanoate.

Analysis calculated for $C_{15}H_{22}O_5Sn$: Percent C, 44.9; H, 5.53; Found: Percent C, 44.77; H, 5.78.

EXAMPLE 8

Flexible Polyurethane Foam

A flexible polyurethane foam-forming reaction mixture was prepared consisting of the following ingredients in the indicated proportions:

| Ingredients | Amount |
| --- | --- |
| Oxypropylated glycerin (mol. wt. 3,000) | 100.0 gms. |
| Silicone surfactant DC-192* | 1.5 mls. |
| 1,4-Diazabicyclo [2.2.2] octane** | 0.3 mls. |
| Water | 4.0 mls. |
| Stannous gel catalyst | 1.0 gms. |
| Toluene diisocyanate (80/20 mixture of 2,4 and 2,6 isomers) | 41.0 mls. |

*Dow Corning 192. This surfactant is a block copolymer of polydimethylsiloxane and a polyether resin.
**33% solution in dipropylene glycol.

In a formulation, the stannous catalyst used, [1,2-benzenediolato (2-)] tin (II), was ground and dispersed at ambient temperature in the oxypropylated glycerin. Water, the surfactant and 1,4-diazabicyclo [2.2.2] octane were then added and blended together by stirring. Toluene diisocyanate was then added and after a final brief blending the mixture was poured into an open-top form whereupon foaming of the reaction mixture occurred. The peak of foam rise occurred 58 seconds after the addition of toluene diisocyanate. The gel time of the foam was 5 seconds later as determined by resistance to penetration by probing with a rod. A foam having a tack-free surface was obtained after curing in an oven at 120° C for 15 minutes. When cut open, this foam exhibited no splits, nor void cavities and no closed cell membranes were visible.

EXAMPLE 9

Flexible Polyurethane Foam

Using the formulation and procedure of Example 8, 1.0 g. of a mixture of 95% of [2-hydroxy-3-methoxyphenolato (1-)] tin (II) octanoate and 5% of [2-hydroxy-6-methoxyphenolato (1-)] tin (II) octanoate was used as the gel catalyst. The peak of the foam rise occurred 65 seconds after the addition of toluene diisocyanate. The gel time of the foam was determined to be about 5 seconds later. A foam having a tack-free surface was obtained after curing in an oven at 110° C for 15 minutes.

EXAMPLE 10

Flexible Polyurethane Foam

The formulation and procedure of Example 8, were used in which 1 g. of [3,4,5,6-tetrabromo-1,2-benzenediolato (2-)] tin (II) was employed as the gel catalyst. The peak of the foam rise occurred 80 seconds after the addition of the toluene diisocyanate. Gel time of the foam was 10 seconds later. A foam having a tack-free surface was obtained after curing in an oven at 110° C for 15 minutes.

EXAMPLE 11

Flexible Polyurethane Foam

Employing the formulation of Example 8, 1 g. of [4-nitro-1,2-benzenedialato (2-)] tin (II) was dispersed in the oxypropylated glycerine. In addition, 1 g. of N-methyl morpholine was added to the water, surfactant and 1,4-diazabicyclo [2.2.2] octane and blended together by stirring. Toluene diisocyanate was then added and after a final brief blending, the foam was produced as in Example 8. The peak of the foam rise occurred 100 seconds after the addition of the toluene diisocyanate. The gel time of the foam was determined to be about 45 seconds later. After curing at 110° C for 15 minutes a foam having a tack-free surface was obtained.

What is claimed is:

1. In a process for preparing a polyurethane foam from a reaction mixture comprising an organic polyisocyanate, a polyol, a blowing agent, and a gel catalyst, the improvement wherein said gel catalyst is a stannous catechol derivative of the formula selected from the group consisting of:

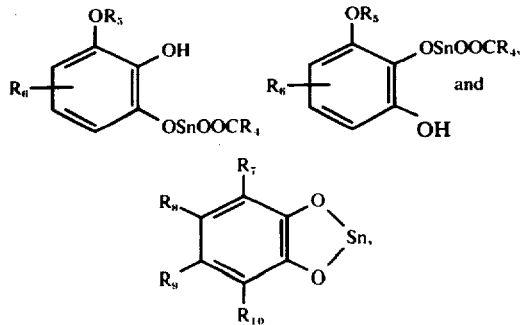

and mixtures thereof,
wherein, $R_4$ represents an alkyl group having from 1 to about 9 carbon atoms or an alkenyl group having from 1 to about 9 carbon atoms, $R_5$ represents an alkyl group having from 1 to about 10 carbon atoms, $R_6$ represents a substituent selected from the group consisting of hydrogen, halogen, nitro and alkyl having 1 to about 10 carbon atoms, and $R_7$, $R_8$, $R_9$ and $R_{10}$ represent substituents independently selected from the group consisting of hydrogen, halogen amine, nitro, nitroso, sulfonyl and alkyl having 1 to about 10 carbon atoms.

2. The process of claim 1 wherein said polyol is an oxyalkylated polyhydric alcohol having a molecular weight of about 2,000 to about 7,000 and said polyurethane foam is a flexible foam.

3. The process of claim 2 wherein said organic polyisocyanate is toluene diisocyanate.

4. A polyurethane foam produced by the process of claim 3.

5. The process of claim 1 wherein said stannous catechol derivative is of the formula selected from the group consisting of:

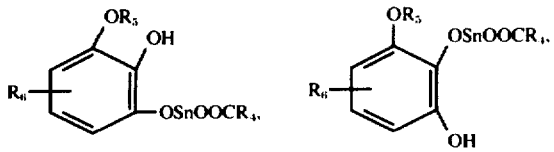

and mixtures thereof,
wherein, in each of said formulas $R_4$ represents an alkyl group having from 1 to about 9 carbon atoms or an alkenyl group having from 1 to about 9 carbon atoms, $R_5$ represents an alkyl group having from 1 to about 10 carbon atoms, and $R_6$ represents a substituent selected from the group consisting of hydrogen, halogen, nitro and alkyl having 1 to about 10 carbon atoms.

6. The process of claim 5 wherein each of said formulas $R_4$ represents an alkyl group having from about 5 to about 9 carbon atoms, and $R_5$ represents an alkyl group having from 1 to about 4 carbon atoms.

7. The process of claim 6 wherein said stannous catechol derivative is selected from the claim consisting of:
[2-hydroxy-3-methoxyphenolato (1-)] tin II octanoate,
[2-hydroxy-6-methoxyphenolato (1-)] 2-hexanoate,
[2-hydroxy-3-methoxyphenolato (1)] tin (II) 2-ethyl hexanoate,
[2-hydroxy-6-methoxyphenolato (1)] tin (II) octanoate, and
[2-hydroxy-3-ethoxyphenolato (1-)] tin (II) hexanoate, and mixtures thereof.

8. The process of claim 7 wherein said polyol is an oxyalkylated polyhydric alcohol having a molecular weight of from about 2,000 to about 7,000 and said polyurethane foam is a flexible foam.

9. The process of claim 8 wherein said organic polyisocyanate is toluene diisocyanate.

10. A polyurethane foam produced by the process of claim 9.

11. The process of claim 7 wherein said stannous catechol derivative is selected from the group consisting of:

[2-hydroxy-3-methoxyphenolato (1-)] tin II octanoate,

[2-hydroxy-6-methoxyphenolato (1-)] tin (II) octanoate, and mixtures thereof.

12. The process of claim 1 wherein said stannous catechol derivative is represented by the formula:

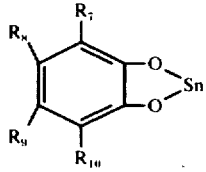

wherein $R_7$, $R_8$, $R_9$ and $R_{10}$ represent a substituent independently selected from the group consisting of hydrogen, halogen, nitro, and alkyl having 1 to about 4 carbon atoms.

13. The process of claim 12 wherein $R_7$, $R_8$, $R_9$ and $R_{10}$ represent a substituent independently selected from the group consisting of hydrogen, chlorine, bromine, nitro and alkyl having from 1 to about 3 carbon atoms.

14. The process of claim 13 wherein said polyol is an oxyalkylated polyhydric alcohol having a molecular weight of from about 2,000 to about 7,000 and said polyurethane foam is a flexible foam.

15. The process of claim 14 wherein said organic polyisocyanate is toluene diisocyanate.

16. A polyurethane foam produced by the process of claim 15.

17. The process of claim 15 wherein said stannous catechol derivative is selected from the group consisting of [1,2-benzenediolato (2-)] tin (II), [3,4,5,6-tetrabromo-1,2-benzenediolato (2-)] tin (II), and [4-nitro-1,2-benzenediolato (2-)] tin (II).

* * * * *